United States Patent [19]

Hanifin, Jr. et al.

[11] 4,197,310

[45] Apr. 8, 1980

[54] THIOPHENEPROPIONITRILES

[75] Inventors: John W. Hanifin, Jr., Suffern; David N. Ridge, Upper Grandview, both of N.Y.

[73] Assignee: American Cyanamid Company, Stamford, Conn.

[21] Appl. No.: 34,315

[22] Filed: Apr. 30, 1979

[51] Int. Cl.$^2$ ..................... A61K 31/38; C07D 333/16
[52] U.S. Cl. ........................................ 424/275; 549/72
[58] Field of Search .................. 424/275; 260/332.3 C

[56] References Cited

U.S. PATENT DOCUMENTS 2,566,665   9/1951   Huffman ...................... 260/332.3 C
2,864,852  12/1958   Jones .......................... 260/332.3 C Primary Examiner—Alan Siegel
Attorney, Agent, or Firm—Edward A. Conroy, Jr.

[57] ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the novel active ingredients of said compositions of matter being certain substituted cis-2-[2(or 3)-thenoyl]-3-hydroxy-2-alkenenitriles and/or the pharmacologically acceptable cationic salts thereof.

14 Claims, No Drawings

THIOPHENEPROPIONITRILES

BRIEF SUMMARY OF THE INVENTION

This invention relates to new organic compounds and, more particularly, is concerned with novel substituted cis-2-[2-(or 3)-thenoyl]-3-hydroxy-2-alkenenitriles and the pharmacologically acceptable cationic salts thereof which may be represented by the following structural formula:

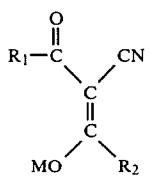

wherein M is hydrogen or a pharmaceutically acceptable cation, $R_2$ is alkyl having from 1 to 4 carbon atoms, and $R_1$ is a 2-thienyl or 3-thienyl moiety of the formulae:

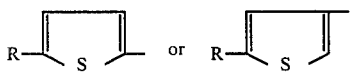

wherein R is hydrogen, alkyl having from 1 to 3 carbon atoms, fluoro, chloro or bromo. The useful pharmaceutically acceptable salts of the compounds of the above structural formula wherein M is hydrogen are those with pharmacologically acceptable metal cations, ammonium or amine cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron, and in particular copper, are within the scope of the invention. Pharmacologically acceptable amine cations are those derived from primary, secondary or tertiary amines such as trimethylamine, ethylamine, dibutylamine, triisopropylamine, allylamine, crotylamine, cyclopentylamine, dicyclohexylamine, benzylamine, β-phenylethylamine, ethylenediamine, diethylenetriamine, as well as heterocyclic amines, e.g. piperidine, morpholine, pyrrolidine, piperazine and lower alkyl derivatives thereof such as 1-methylpiperidine, 4-ethylmorpholine, 1-isopropylpyrrolidine, 1,4-dimethylpiperazine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, and the like.

The cis-2-[2(or 3)-thenoyl]-3-hydroxy-2-alkenenitriles of the present invention may exist in other tautomeric forms as follows:

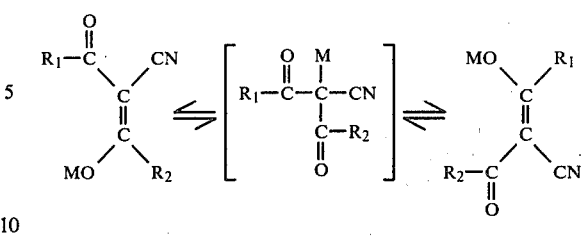

DETAILED DESCRIPTION OF THE INVENTION

Several procedures exist for the attachment of the acyl fragment to a thenoylacetonitrile side chain. The first involves direct acylation of the thenoylacetonitrile anion (1) with an acyl halide (2) in an appropriate solvent to provide the product (3) as set forth in the following reaction scheme wherein Me is a metal cation as hereinabove defined, X is chloro or fluoro, and $R_1$ and $R_2$ are as hereinabove defined:

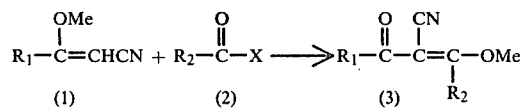

The enolate anions (1) are prepared by the treatment of the thenoylacetonitrile with the appropriate base in an inert solvent. This enolate may be generated in situ and acylated with (2) in the same solvent or may be isolated and reacted in a different solvent system. When Me represents sodium where (1) has been generated by treatment of the thenoylacetonitrile with sodium hydride, sodium amide, sodium methoxide, etc. and X represents chlorine, yields of (3) are low with undesired side products sometimes predominating. Preferably, the thenoylacetonitrile is dissolved in diethyl ether and one equivalent of thallium (I) ethoxide is added. The stable enolate (1), where Me is thallium, precipitates and may be collected by filtration, dried and stored indefinitely. Suspension of (1) in an inert solvent such as diethyl ether, tetrahydrofuran, dioxane, etc. at room temperature and the treatment of same with an acyl fluoride (2) causes precipitation of thallium (I) fluoride. This is removed by filtration and the product is extracted from the filtrate.

Another approach involves addition of the acyl fragment as a hydrolyzable portion to yield (5) as set forth in the following reaction scheme wherein $R_1$ is as hereinabove defined:

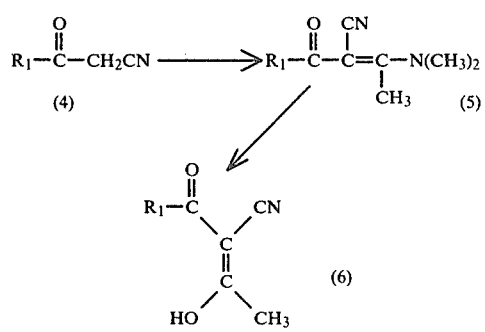

This may be performed by treatment of the thenoylacetonitrile (4) with N,N-dimethylacetamide dimethylacetal at low temperature in chloroform, methylene chloride, or even as a neat mixture of reagents. Purification yields the condensed product (5). Hydrolysis of (5) with dilute aqueous mineral acid provides (6). Alternatively, the thenoylacetonitrile (4) is condensed with a trialkyl orthoester (7) in refluxing acetic anhydride as set forth in the following reaction scheme:

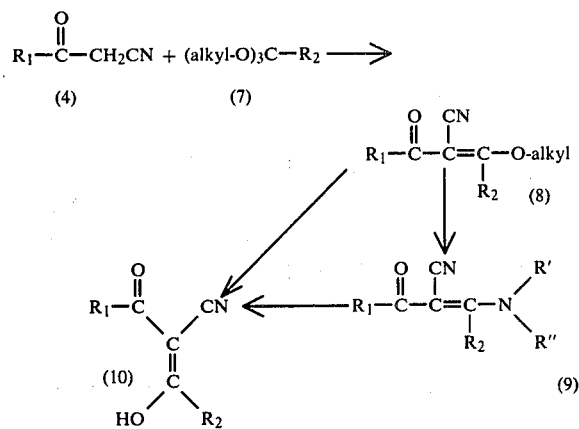

wherein $R_1$ and $R_2$ are as hereinbefore defined, alkyl is methyl or ethyl, R' and R" are each hydrogen or alkyl having up to 4 carbon atoms and R' and R" taken together with the associated N(itrogen) is pyrrolidino, piperidino, morpholino, thiomorpholino or N-methylpiperazino. Evaporation of by-products and excess acetic anhydride in vacuo and purification of the product under anhydrous conditions provides (8). Treatment of (8) with ammonia or a primary or secondary amine at steam bath temperature under pressure in a sealed vessel for 8–12 hours then provides (9). Both of these intermediates (8) and (9) may be hydrolyzed under acidic conditions to provide the desired products (10).

A different approach to (10) wherein $R_2$ is methyl or ethyl involves addition of the cyanoacyl fragment to a 2(or 3)-thenoyl chloride (11) as set forth below wherein R° is methyl or ethyl and R is as hereinabove defined. This may be The novel compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, intra-articular, or subcutaneous route. The anti-inflammatory activity of the novel compounds of the present invention was established by the following tests.

(A) Carrageenin-induced edema in the rat

In determining the acute anti-inflammatory activity of the cis-2-[2(or 3)-thenoyl]-3-hydroxy-2-alkenenitriles of the present invention, Royal Hart, Wistar strain rats, ranging in weight from 80 to 90 grams were used. The rats were fasted overnight prior to dosing but had free access to water. The test compounds were administered in aqueous suspension, by gavage, in a volume of 1.7 ml. per 50 grams of rat [corresponds to hydration volume used by Winter, et al., Proc. Soc. Exp. Biol. & Med., 111, 544–547 (1962)]. The phlogistic agent used was carrageenin prepared as a sterile 1% suspension in 0.9% aqueous sodium chloride for routine testing. A volume of 0.05 ml. was injected through a 26 gauge needle into the plantar tissue of the right hind paw. Measurements were made 5 hours after drug administration (4 hours after carrageenin challenge). Volumes of both the normal and carrageenin inflamed feet were determined. The difference between the two measurements is considered to be the increased edema due to the carrageenin administration. Results are expressed as a C/T efficacy ratio (edema of control animals/edema of treated animals). Table I records the results of this test

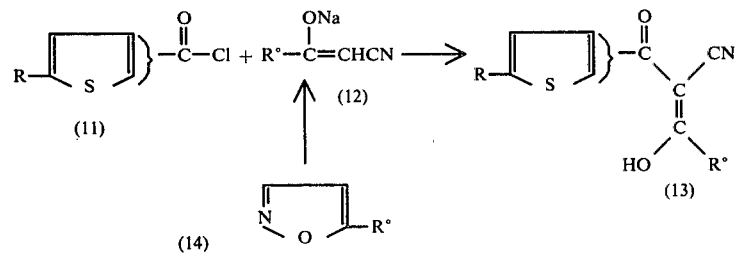

performed by generation of the enolate anion (12) in situ with the 5-alkyl-isoxazole (14) and a base such as sodium hydride or sodium amide and subsequent addition of the 2(or 3)-thenoyl chloride (11) to affect condensation to provide (13). Alternatively, the α-cyanoenolate (12) may be prepared separately in a similar manner as above and isolated. Addition of this enolate to the appropriate 2(or 3)-thenoyl chloride in ether, tetrahydrofuran, etc. at room temperature or at reflux provides (13).

at the indicated dose level with typical compounds of the present invention and demonstrates the anti-inflammatory effect of these compounds in comparison with known anti-inflammatory agents.

Table I

The Effect of Anti-inflammatory Agents on Carrageenin-Induced Edema

| Compound | Number of Rats | C/T Ratio |
|---|---|---|
| Control | 8 | — |
| Aspirin | 8 | 2.86* |
| Cis-2-(2-thenoyl)-3-hydroxy-2-butenenitrile | 6 | 2.04* |
| Cis-2-(3-thenoyl)-3-hydroxy-2-butenenitrile | 7 | 2.42* |

*Statistically significant activity by t test p = <.05

(B) Adjuvant-induced arthritis in the rat

The following test shows the activity of the cis-2-[2(or 3)-thenoyl]-3-hydroxy-2-alkenenitriles of this invention against chronic inflammation in adjuvant induced arthritis which is accompanied by joint destruction. Groups of three Royal Hart, Wistar strain rats weighing 200±10 g. each were injected intradermally in the right hind paw with Freund's adjuvant (dried human tubercle bacilli in a mineral oil vehicle) at a dose of 2 mg./kg. of body weight. The test compounds were administered orally in a 1.5% starch vehicle at various doses once daily on days 0 to 13 post challenge. Control rats were treated in a similar manner, but given only starch vehicle. On the 14th and 21st day post challenge the diameter of the injected paw was measured by micrometer caliper. The volume of inflamed paws were estimated from these measurements and the effects of each compound are expressed as percent inhibition of swelling as compared to controls. Table II records the results of these tests conducted with representative compounds of this invention and known anti-inflammatory agents. The active compounds of this invention suppress the progression of the arthritis and associated joint deterioration.

Table II

The Effect of Anti-Inflammatory Agents on Adjuvant Induced Arthritis in Rats

| Compound | Oral Dose (mg./kg.) | Number of Rats | % Inhibition of Swelling Day 14 | % Inhibition of Swelling Day 21 |
|---|---|---|---|---|
| Normal rats | — | — | — | — |
| Adjuvant Controls | — | 57 | 0 | 0 |
| Indomethacin | 2 | 57 | 51* | 24* |
|  | 1 | 54 | 46* | 19* |
|  | 0.5 | 54 | 40* | 20* |
|  | 0.25 | 9 | 30* | 4 |
| Aspirin | 400 | 57 | 73* | 48* |
|  | 200 | 66 | 48* | 27* |
|  | 100 | 63 | 36* | 13 |
|  | 50 | 21 | 23* | 3 |
| Phenylbutazone | 150 | 27 | 75* | 44* |
|  | 75 | 39 | 62* | 28* |
|  | 37.5 | 39 | 56* | 14 |
|  | 18.8 | 21 | 31* | 7 |
| Cis-2-(2-thenoyl)-3-hydroxy-2-butenenitrile | 50 | 18 | 42 | 6 |
| Cis-2-(3-thenoyl)-3-hydroxy-2-butenenitrile | 50 | 18 | 38* | 19 |
| Cis-2-(5-chloro-2-thenoyl)-3-hydroxy-2-butenenitrile | 25 | 9 | 49* | 31* |

*Statistically significant activity p = <.05 by t test

Adjuvant-induced experimental polyarthritis is a specific systemic disease of the rat which shares interesting similarities with rheumatoid arthritis. Specifically the histology of the two diseases bears a remarkable resemblance as shown by C. M. Pearson et al., Am. J. Path. 42, 73 (1963). E. M. Glenn, Am. J. Vet. Res. 27, (116), 339 (1966) has classified adjuvant-induced polyarthritis as a crippling and permanent deformity resulting from diffuse connective tissue involvement around certain susceptible joints in the rat. Zahiri et al, Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pointed reference showing the relationship between arthritis and joint deterioration is an X-Ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

Compositions according to the present invention having the desired clarity, stability and adaptability for parenteral and intra-articular use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The cis-2-[2(or 3)-thenoyl]-3-hydroxy-2-alkenonitriles are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Cis-2-(2-thenoyl)-3-hydroxycrotononitrile

A 67 ml. portion of ethyl 2-thiophenecarboxylate is added to 56 g. of potassium t-butoxide (exothermic). After cooling, 33 ml. of acetonitrile is added and the mixture is stirred and heated on a steam bath for 1.5 hours. A 250 ml. portion of water is added followed by 200 ml. of methylene chloride. The mixture is stirred overnight. The aqueous layer is separated and combined with 42 ml. of concentrated hydrochloric acid. This mixture is extracted with 300 ml. of methylene chloride followed by two 100 ml. portions of methylene chloride. The combined extracts are then washed with 200 ml. followed by 100 ml. of 10% sodium bicarbonate. The extracts are dried over sodium sulfate and passed through magnesol. The filtrate is combined with hexanes and evaporated giving crystals of β-oxo-2-thiophenepropionitrile.

A 10.0 g. portion of β-oxo-2-thiophenepropionitrile in 100 ml. of chloroform is reacted with 10 ml. of N,N-dimethylacetamide dimethylacetal in an ice bath. The mixture is stirred in an ice bath for 2 hours and then at room temperature overnight. The mixture is evaporated to an oil which is dissolved in 50 ml. of methanol. A 15 ml. portion of 1 N hydrochloric acid is added and the mixture is heated on a steam bath for ½ hour. Evaporation produces an oil which is combined with 75 ml. of benzene and 75 ml. of saturated aqueous sodium bicarbonate and mixed. The aqueous phase is saved. The organic phase is washed three times with saturated aqueous sodium bicarbonate. The aqueous phases are combined, washed twice with 100 ml. of benzene, and acidified with concentrated hydrochloric acid and the solid is collected. This solid is dried, dissolved in 50 ml. of hot isopropanol, treated with charcoal and cooled giving the desired product as a solid, m.p. 106°–108° C.

EXAMPLE 2

Cis-2-(3-thenoyl)-3-hydroxycrotononitrile

A 50 ml. portion of quinoline is added to a mixture of 35 g. of cuprous cyanide and 50 g. of 3-bromothiophene. The mixture is warmed slowly with stirring until a solution forms and then heated at 190° C. for one hour. The mixture is poured into water, 200 ml. of concentrated ammonium hydroxide is added and the solid residue is extracted five times with diethyl ether. The combined ether extracts are dried, treated with charcoal, filtered and evaporated to a brown liquid. This liquid is distilled, collecting four fractions which are combined, dissolved in diethyl ether, washed twice with 4 N hydrochloric acid, water and saturated sodium chloride solution, dried and evaporated giving 27.7 g. of 3-cyanothiophene.

A 113 g. portion of potassium t-butoxide is added to 800 ml. of diethyl ether. To this is added a mixture of 110.6 g. of 3-cyanothiophene and 54 ml. of acetonitrile in 350 ml. of ether. The reaction mixture is stirred in an ice-salt bath, more ether is added and the mixture is shaken vigorously. After standing for one hour at room temperature the mixture is poured into one liter of water. The layers are separated. The aqueous phase is extracted with diethyl ether. The ether phases are combined, washed with water and evaporated. The residue is dissolved in benzene, dried over magnesium sulfate and evaporated. To the residue is added 200 ml. of benzene and some petroleum ether. The mixture is cooled and the precipitate is collected and saved. The mother liquor is filtered through Magnesol ®, evaporated and petroleum ether is added. Cooling produces a precipitate which is collected, dissolved in hot benzene, treated with charcoal and cooled giving a precipitate which is collected and combined with the first precipitate. The combined precipitates are recrystallized twice from hot benzene and charcoal giving 29.6 g. of β-amino-3-thiopheneacrylonitrile.

A 2.5 g. portion of the β-amino-3-thiopheneacrylonitrile is combined with 20 ml. of 1 N hydrochloric acid and sufficient methanol to produce solution. The mixture is stirred at room temperature for ½ hour, evaporated to ½ volume, cooled and the precipitate is collected. This solid is recrystallized with charcoal treatment from 30 ml. of hot isopropanol giving 2.4 g. of β-oxo-3-thiophenepropionitrile.

A 1.5 g. portion of β-oxo-3-thiophenepropionitrile in 25 ml. of chloroform is reacted with 1.5 ml. of N,N-dimethylacetamide dimethylacetal as described in Example 1, giving the desired product as a solid, m.p. 74°–76° C.

EXAMPLE 3

Cis-2-(5-chloro-2-thenoyl)-3-hydroxycrotononitrile

A 50 g. portion of 5-chloro-2-thiophenecarboxaldehyde, 27.6 g. of hydroxylamine hydrochloride, 43.1 g. of sodium formate and 500 ml. of formic acid are reacted to produce 5-chloro-2-cyanothiophene.

A mixture of 32.4 g. of potassium t-butoxide in 600 ml. of toluene is cooled in an ice bath. A solution of 37.9 g. of 5-chloro-2-cyanothiophene and 21.0 ml. of acetonitriel diluted to 150 ml. with toluene is added dropwise, with rapid stirring over a one hour period. The mixture is stirred at room temperature overnight. One liter of water is added. The mixture is stirred for ½ hour. The aqueous layer is extracted with three 250 ml. portions of diethyl ether which are combined, dried over magnesium sulfate and concentrated almost to dryness. The residue is dissolved in a minimum of hot toluene, treated with charcoal and cooled. Petroleum ether is added, the mixture is chilled and the precipitate is collected as crystals of β-amino-5-chloro-2-thiopheneacrylonitrile.

A 9.2 g. portion of β-amino-5-chloro-2-thiopheneacrylonitrile is dissolved in 100 ml. of methanol. A 50 ml. portion of 1 N hydrochloric acid is added and the mixture is stirred at room temperature for 3 hours. The precipitate is collected giving 5-chloro-β-oxo-2-thiophenepropionitrile.

A 9.8 g. portion of 5-chloro-β-oxo-2-thiophenepropionitrile in 75 ml. of chloroform is reacted with 9.0 ml. of N,N-dimethylacetamide dimethylacetal as described in Example 1 giving the desired product, m.p. 103°–105° C.

EXAMPLE 4

Preparation of 50 mg. Tablets

| Per Tablet | | Per 10,000 Tablets |
|---|---|---|
| 0.050 gm. | Cis-2-(5-fluoro-2-thenoyl)-3-hydroxycrotonitrile | 500 gm. |
| 0.080 gm. | Lactose | 800 gm. |
| 0.010 gm. | Corn Starch (for Mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The cis-2-(5-fluoro-2-thenoyl)-3-hydroxycrotonitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 5

Preparation of Oral Suspension

| Ingredient | Amount |
|---|---|
| Cis-2-(5-fluoro-3-thenoyl)-3-hydroxy-2-pentenenitrile | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water . . . qs . . . ad | 100 mg |

The sorbitol solution is added to 40 ml. of distilled water and the cis-2-(5-fluoro-3-thenoyl)-3-hydroxy-2-pentenenitrile is suspended therein. The saccharin, sodium benzoate, flavor and dye are added and dissolved. The volume is adjusted to 100 ml. with distilled water. Each ml. of syrup contains 5 mg. of cis-2-(5-fluoro-3-thenoyl)-3-hydroxy-2-pentenenitrile.

EXAMPLE 6

Preparation of Patenteral Solution

In a solution of 700 ml. of propylene glycol and 200 ml. of water for injection is suspended 20.0 grams of cis-3-hydroxy-2-(5-bromo-2-thenoyl)crotononitrile with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 7

Preparation of Topical Cream

| Ingredient | Amount |
|---|---|
| Cis-2-(5-bromo-3-thenoyl)-3-hydroxy-4-methyl-2-pentenenitrile | 1.0% |
| Ethoxylated Stearyl alcohol | 10.0% |
| Benzyl alcohol | 0.9% |
| Isopropyl palmitate | 5.0% |
| Sorbitol solution (USP) | 5.0% |
| Glycerin | 5.0% |
| Lactic acid    qs    to    pH 4.0–5.0 | |
| Water    qs    ad | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°–75° C. The cis-2-(5-bromo-3-thenoyl)-3-hydroxy-4-methyl-2-pentenenitrile is added to the wax phase and the mixture-is stirred until a clear solution is obtained. The benzyl alcohol is added and dissolved in the wax phase. The water phase is passed through a screen into the wax phase while maintaining agitation. Both phases are kept at about the same temperature during transfer. The mixture is cooled while agitation is continued. At a temperature of 50°–55° C. the balance of the water is added. The pH is adjusted to 4.0–5.0 with

EXAMPLE 8

Preparation of Intra-articular Product

| Ingredient | Amount |
| --- | --- |
| Cis-2-(5-chloro-3-thenoyl)-3-hydroxy-2-heptenenitrile | 2–20 mg. |
| NaCl (physiological saline) | 0.9% |
| Benzyl alcohol N.F. | 0.9% |
| Sodium carboxymethylcellulose | 1–5% |
| pH adjusted to 5.0–7.5 | |
| Water for injection . . . qs ad | 100% | lactic acid. The batch is cooled with minimum agitation until the cream sets in its final form.

EXAMPLE 9

β-Oxo-2-thiophenepropionitrile, thallium (I) salt

A solution of 10 g. of β-oxo-2-thiophenepropionitrile in 150 ml. of diethyl ether is stirred at 25° C. while 17.2 g. of neat thallium (I) ethoxide is added dropwise. The mixture is stirred as a colorless precipitate forms. After one hour, the mixture is filtered and the precipitate is washed with diethyl ether. Upon air-drying, 21.3 g. of colorless thallium (I) salt is obtained.

Similarly prepared are the thallium (I) salts of β-oxo-3-thiophenepropionitrile and 5-chloro-β-oxo-2-thiophenepropionitrile.

EXAMPLE 10

Cis-2-(2-thenoyl)-3-hydroxycrotononitrile

A suspension of 5.5 g. of β-oxo-2-thiophenepropionitrile, thallium (I) salt in 50 ml. of tetrahydrofuran is stirred at room temperature as acetyl fluoride is bubbled through. After 3 hours, the gas flow is stopped, the reaction vessel is stoppered and the mixture is allowed to stand overnight. After 24 hours, the mixture is filtered and the filtrate is evaporated to dryness. Recrystallization of the residue from chloroform/hexane provides the title compound.

Similarly prepared are cis-2-(3-thenoyl)-3-hydroxycrotononitrile and cis-2-(5-chloro-2-thenoyl)-3-hydroxycrotononitrile.

EXAMPLE 11

Cis-2-(2-thenoyl)-3-hydroxycrotononitrile

A solution of 10 g. of β-oxo-2-thiophenepropionitrile, 10.7 g. of triethyl orthoacetate and 20 ml. of acetic anhydride is heated on a steam bath for 12 hours, then cooled and the excess acetic anhydride is evaporated under reduced pressure. The residue is treated with 50 ml. of ethanol and 50 ml. of 1 N aqueous hydrochloric acid. After one hour, the solution is diluted with water and the product extracted with methylene chloride. The organic phase is washed with three portions of aqueous sodium bicarbonate which are combined, acidified, and extracted with methylene chloride. This organic phase is dried and evaporated. The crude residue is recrystallized from chloroform/hexane to provide the title compound.

Similarly, cis-2-(2-thenoyl)-3-hydroxy-2-pentenenitrile is prepared from β-oxo-2-thiophenepropionitrile and triethyl orthopropionate.

EXAMPLE 12

Cyanoacetone, sodium salt

A solution of 0.174 mole of sodium ethoxide is prepared by dissolving 4.0 g. of sodium in 200 ml. of absolute ethanol. A neat sample of 15 ml. (0.184 mole) of 5-methylisoxazole is added dropwise as a colorless precipitate forms. When the addition is complete, the mixture is cooled in an ice bath and then filtered. The precipitate is collected and washed with hexane, yielding 14.0 g. of colorless product.

EXAMPLE 13

Cis-2-(3-thenoyl)-3-hydroxycrotononitrile

A neat sample of 20.0 g. of 3-thiophenecarboxylic acid was added dropwise to 50 ml. of thionyl chloride. The solution was stirred at room temperature overnight and the excess thionyl chloride was then evaporated under reduced pressure. The residue was vacuum distilled to provide 21.2 g. of 3-thiophenecarboxylic acid chloride.

A mixture of 19.0 g. of cyanoacetone, sodium salt in 200 ml. of dry tetrahydrofuran is stirred while 10.0 g. of 3-thiophenecarboxylic acid chloride in 75 ml. of tetrahydrofuran is added dropwise. The reaction mixture is stirred overnight and then most of the solvent is evaporated under reduced pressure. The residue is acidified and extracted with chloroform. The organic phase is washed three times with aqueous sodium bicarbonate and the combined basic washes are acidified. The resulting mixture is extracted with methylene chloride. Evaporation of the organic layer and recrystallization of the residue provides the title compound.

EXAMPLE 14

Cis-2-(3-thenoyl)-3-hydroxycrotononitrile

An 8.0 g. portion of diisopropylamine in 100 ml. of diethyl ether is cooled to 0° C. under argon. A solution of 31.5 ml. of 2.5 M n-butyllithium in hexane is added dropwise and the reaction is further cooled to −10° C. A 5.94 g. portion of 5-methylisoxazole is then added dropwise and the mixture is stirred for ½ hour. A 10.5 g. portion of 3-thiophenecarboxylic acid chloride is added while the reaction is held at 0° C. The mixture is allowed to warm to room temperature and stand for 18 hours. The reaction is quenched with water, acidified with dilute hydrochloric acid and extracted with chloroform. The chloroform phase is extracted three times with aqueous sodium bicarbonate and the combined aqueous extracts are acidified and washed three times with chloroform. The organic extract is dried, filtered and evaporated. The residue is recrystallized from ethanol-hexane giving the desired compound.

EXAMPLE 15

Cis-2-(5-methyl-3-thenoyl)-3-hydroxy-2-hexenenitrile

The general procedure of Example 11 is repeated but replacing the β-oxo-2-thiophenepropionitrile and triethyl orthoacetate employed in that example with equivalent amounts of 5-methyl-β-oxo-3-thiophenepropionitrile and triethyl orthobutyrate whereby there is obtained the title compound in equally good yield.

EXAMPLE 16

5-Methyl-2-thiophene carbonyl chloride

Heating 100 g. of 5-methyl-2-thiophenecarboxylic acid in 130 ml. of thionyl chloride at 100° C. for 1½ hours followed by distillation gave 112.26 g. (99.3%) of 5-methyl-2-thiophene carbonyl chloride, which boiled at 108°–110° C./13 mm.

EXAMPLE 17

Cis-2-(5-methyl-2-thenoyl)-3-hydroxycrotononitrile

A mixture of 0.05 mole (8.03 g.) of 5-methyl-2-thiophene carbonyl chloride and 0.15 mole (15.76 g.) of cyanoacetone sodium enolate in 100 ml. of tetrahydrofuran was stirred for 3 hours. After removal of the tetrahydrofuran in vacuo, the residue was slurried with water, acidified with hydrochloric acid, and extracted into methylene chloride. The methylene chloride extracts were, in turn, extracted with two 50 ml. portions of saturated sodium bicarbonate. The combined bicarbonate extracts were treated with Darco ® and acidified to give, after recrystallization from isopropanol, 5.19 g. (50%) of the desired product as a light yellow crystalline solid melting at 71°–73° C.

We claim:

1. A compound selected from the group consisting of those of the formula:

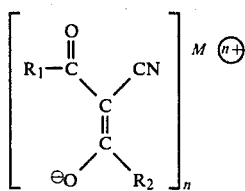

wherein $R_1$ is a thienyl moiety selected from the group consisting of those of the formulae:

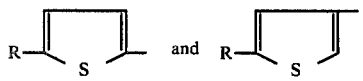

wherein R is hydrogen, alkyl having up to 3 carbon atoms, fluoro, chloro or bromo; $R_2$ is alkyl having up to four carbon atoms; n is an integer from 1 to 3, inclusive, and M is hydrogen or a pharmacologically acceptable cation; and the tautomers thereof.

2. The compound according to claim 1 wherein M is hydrogen, n is 1, $R_1$ is 2-thienyl and $R_2$ is methyl; cis-2-(2-thenoyl)-3-hydroxycrotononitrile.

3. The compound according to claim 1 wherein M is hydrogen, n is 1, $R_1$ is 3-thienyl and $R_2$ is methyl; cis-2-(3-thenoyl)-3-hydroxycrotononitrile.

4. The compound according to claim 1 wherein M is hydrogen, n is 1, $R_1$ is 5-chloro-2-thienyl and $R_2$ is methyl; cis-2-(5-chloro-2-thenoyl)-3hydroxycrotononitrile.

5. The compound according to claim 1 wherein M is triethylammonium, n is 1, $R_1$ is 2-thienyl and $R_2$ is methyl; cis-2-(b 2-thenoyl)-3-hydroxycrotononitrile, triethylamine salt.

6. The compound according to claim 1 wherein M is sodium, n is 1, $R_1$ is 5-fluoro-3thienyl and $R_2$ is ethyl; cis-2-(5-fluoro-3-thenoyl)-3-hydroxy-2-pentenenitrile, sodium salt.

7. The compound according to claim 1 wherein M is cupric, n is 2, $R_1$ is 5-methyl-2-thienyl and $R_2$ is isopropyl; cis-2-(5-methyl-2-thenoyl)-3-hydroxy-4-methyl-2-pentenenitrile, copper (II) salt.

8. The compound according to claim 1 wherein M is hydrogen, n is 1, $R_1$ is 5-fluoro-2-thienyl and $R_2$ is isobutyl; cis-2-(5-fluoro-2-thenoyl)-3-hydroxy-5-methyl-2-hexenenitrile.

9. The compound according to claim 1 wherein M is hydrogen, n is 1, $R_1$ is 5-chloro-3-thienyl and $R_2$ is methyl; cis-2-(5-chloro-3-thenoyl)-3-hydroxycrotononitrile.

10. The compound according to claim 1 wherein M is hydrogen, n is 1, $R_1$ is 5-isopropyl-3-thienyl and $R_2$ is ethyl; cis-2-(5-isopropyl-3-thenoyl)-3-hydroxy-2-pentenenitrile.

11. The method of inhibiting the progression of arthritis in a mammal which comprises administering to said mammal an effective amount of a compound selected from the group consisting of those of the formula:

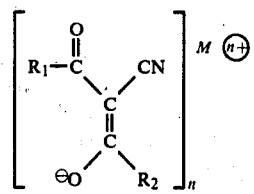

wherein $R_1$ is a thienyl moiety selected from the group consisting of those of the formulae:

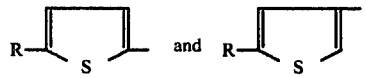

wherein R is hydrogen, alkyl having up to 3 carbon atoms, fluoro, chloro or bromo; $R_2$ is alkyl having up to four carbon atoms; n is an integer from 1 to 3, inclusive, and M is hydrogen or a pharmacologically acceptable cation; and the tautomers thereof.

12. The method of inhibiting progressive joint deterioration in a mammal which comprises administering to said mammal an effective amount of a compound selected from the group consisting of those of the formula:

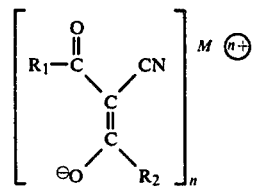

wherein $R_1$ is a thienyl moiety selected from the group consisting of those of the formulae:

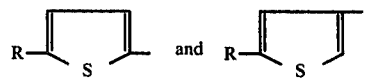

wherein R is hydrogen, alkyl having up to 3 carbon atoms, fluoro, chloro or bromo; $R_2$ is alkyl having up to four carbon atoms; n is an integer from 1 to 3, inclusive, and M is hydrogen or a pharmacologically acceptable cation; and the tautomers thereof.

13. The method of meliorating inflammation in a mammal which comprises administering to said mammal an effective amount of a compound selected from the group consisting of those of the formula:

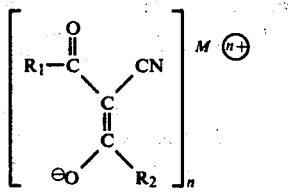

wherein $R_1$ is a thienyl moiety selected from the group consisting of those of the formulae:

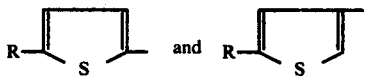

wherein R is hydrogen, alkyl having up to 3 carbon atoms, fluoro, chloro or bromo; $R_2$ is alkyl having up to four carbon atoms; n is an integer from 1 to 3, inclusive, and M is hydrogen or a pharmacologically acceptable cation; and the tautomers thereof.

14. An anti-arthritic composition in dosage unit form useful for meliorating the inflammation and/or the progressive joint deterioration characteristic of arthritic disease in mammals comprising from about one milligram to about 250 milligrams per kilogram of body weight per daily dosage unit of a compound selected from the group consisting of those of the formula:

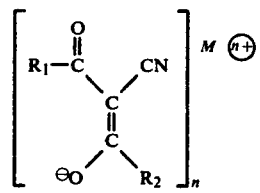

wherein $R_1$ is a thienyl moiety selected from the group consisting of those of the formulae:

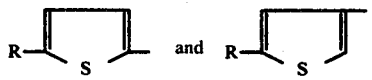

wherein R is hydrogen, alkyl having up to 3 carbon atoms, fluoro, chloro or bromo; $R_2$ is alkyl having up to four carbon atoms; n is an integer from 1 to 3, inclusive, and M is hydrogen or a pharmacologically acceptable cation; and the tautomers thereof; in association with a pharmaceutical carrier.

* * * * *